United States Patent [19]
Witt et al.

[11] 4,403,184
[45] Sep. 6, 1983

[54] AUTOCORRELATION APPARATUS AND METHOD FOR APPROXIMATING THE OCCURRENCE OF A GENERALLY PERIODIC BUT UNKNOWN SIGNAL

[75] Inventors: Rüdiger Witt, Holzgerlingen; Erich Courtin, Herrenberg-Gültstein, both of Fed. Rep. of Germany

[73] Assignee: Hewlett-Packard Company, Palo Alto, Calif.

[21] Appl. No.: 359,393

[22] Filed: Mar. 18, 1982

Related U.S. Application Data

[63] Continuation of Ser. No. 20,768, Mar. 15, 1979, abandoned.

[30] Foreign Application Priority Data

Apr. 28, 1978 [DE] Fed. Rep. of Germany ....... 2818768

[51] Int. Cl.³ ..................... G01R 23/02; G01R 19/04; A61B 5/02
[52] U.S. Cl. ................................. 324/78 R; 128/660; 128/695; 324/77 G
[58] Field of Search ............... 324/78 R, 77 G, 103 P; 128/660, 661, 695, 696, 706

[56] References Cited

U.S. PATENT DOCUMENTS

| 3,896,375 | 7/1975 | Trolliet | 324/103 P |
| 3,991,365 | 11/1976 | Takeuchi | 324/78 R |
| 4,037,151 | 7/1977 | Takeuchi | 324/78 R |
| 4,187,461 | 2/1980 | Cox | 324/103 P |

FOREIGN PATENT DOCUMENTS

| 1766387 | 7/1971 | Fed. Rep. of Germany ... 324/103 P |
| 2364733 | 7/1974 | Fed. Rep. of Germany ... 324/103 P |
| 2803356 | 8/1978 | Fed. Rep. of Germany ... 324/103 P |

*Primary Examiner*—Gerard R. Strecker
*Attorney, Agent, or Firm*—Edward L. Miller

[57] ABSTRACT

A method and an apparatus for indicating in real time the occurrence of and measuring the frequency or period of the basic oscillation of a generally periodic unknown signal with statistically distributed spectral components is disclosed. Using an autocorrelation technique, the time interval from the initial peak value to the next successive peak value of the autocorrelation curve is measured and the unknown frequency or period is determined therefrom. A periodically occurring maximum of the next successive peak value is determined, and, on its appearance, a signal is produced, said signal approximating the occurrence in real time of the generally periodic signal.

4 Claims, 10 Drawing Figures

AUTOCORRELATION APPARATUS AND METHOD FOR APPROXIMATING THE OCCURRENCE OF A GENERALLY PERIODIC BUT UNKNOWN SIGNAL

REFERENCE TO RELATED APPLICATION

This is a continuation of an earlier filed and co-pending application Ser. No. 20,768 by the same inventors filed Mar. 15, 1979 and orginally titled METHOD AND APPARATUS FOR MEASURING THE FREQUENCY OF PERIOD OF A SIGNAL, which application is now abandoned.

BACKGROUND OF THE INVENTION

Circuits to produce an indication or output signal in synchronism with an input signal are well known. For example, the horizontal sweep trigger circuit of an oscilloscope performs such a function based upon the input signal achieving a certain amplitude or perhaps exhibiting a certain minimum rate of change. Such applications often require that the input signal be a separate signal free of nonrelated signals and have a reasonable signal to noise ratio as well.

Consider, however, the task of producing an indication or output signal in synchronism with a generally periodic complex signal amid unrelated other signals in a noisy environment. Say, for instance, one needed to isolate the sound of dripping water from a leaky faucet amid the sound of a radio playing in the background, and produce an indication synchronized with the individual drops. Or, suppose the task were to isolate, measure the frequency of, and provide a real time indication of each occurrence of a fetal heat beat within the uterus. Autocorrelation techniques are highly useful in such circumstances to provide frequency information for the signal to be isolated. However, such frequency information does not contain a real time indication of when the signal actually occurs.

The present invention deals with a process or a device for the measurement of the frequency or period of the basic oscillation of an approximately periodic signal with statistically distributed spectral components using autocorrelation.

Such a process and such a device are known from German Laid-Open Patent Application 25 46 856. Accordingly, it is possible to determine exactly the frequency or period of a frequency in real time, that is, essentially, to display its duration immediately upon termination of the period. In this way, in particular using the Doppler principle, ultrasonic signals obtained from the fetal heart beat can be employed as the basis for an accurate measurement of the heartbeat rate. The employment of the correlation technique for the improvement of the measurement of the heart rate is, however, associated with the disadvantage that, when carrying out autocorrelation, the phase information on the heartbeat is lost. In consequence neither a beat-to-beat display of the heart rate, nor a visual or acoustic beat display is possible.

SUMMARY OF THE INVENTION

It is an object of the present invention to improve the process or device of the type mentioned, so that a real time display of the instantaneous beating of the fetal heart becomes possible.

According to the invention a method and an apparatus for measuring the frequency or period of the basic oscillation of an approximately periodic signal with statistically distributed spectral components using the autocorrelation is provided, where the time interval from the initial peak value to the next successive peak value of the autocorrelation curve thus obtained is measured and the frequency or the period of the basic oscillation is determined from this time interval. The maximum in time of the next successive peak value is also determined and, on its appearance, a signal is produced indicating a real time the occurrence of a characteristic point in the approximately periodic signal, e.g. the occurrence of the heartbeat when the approximately periodic signal is a heart signal.

DESCRIPTION OF THE PREFERRED EMBODIMENT

Figure 1:
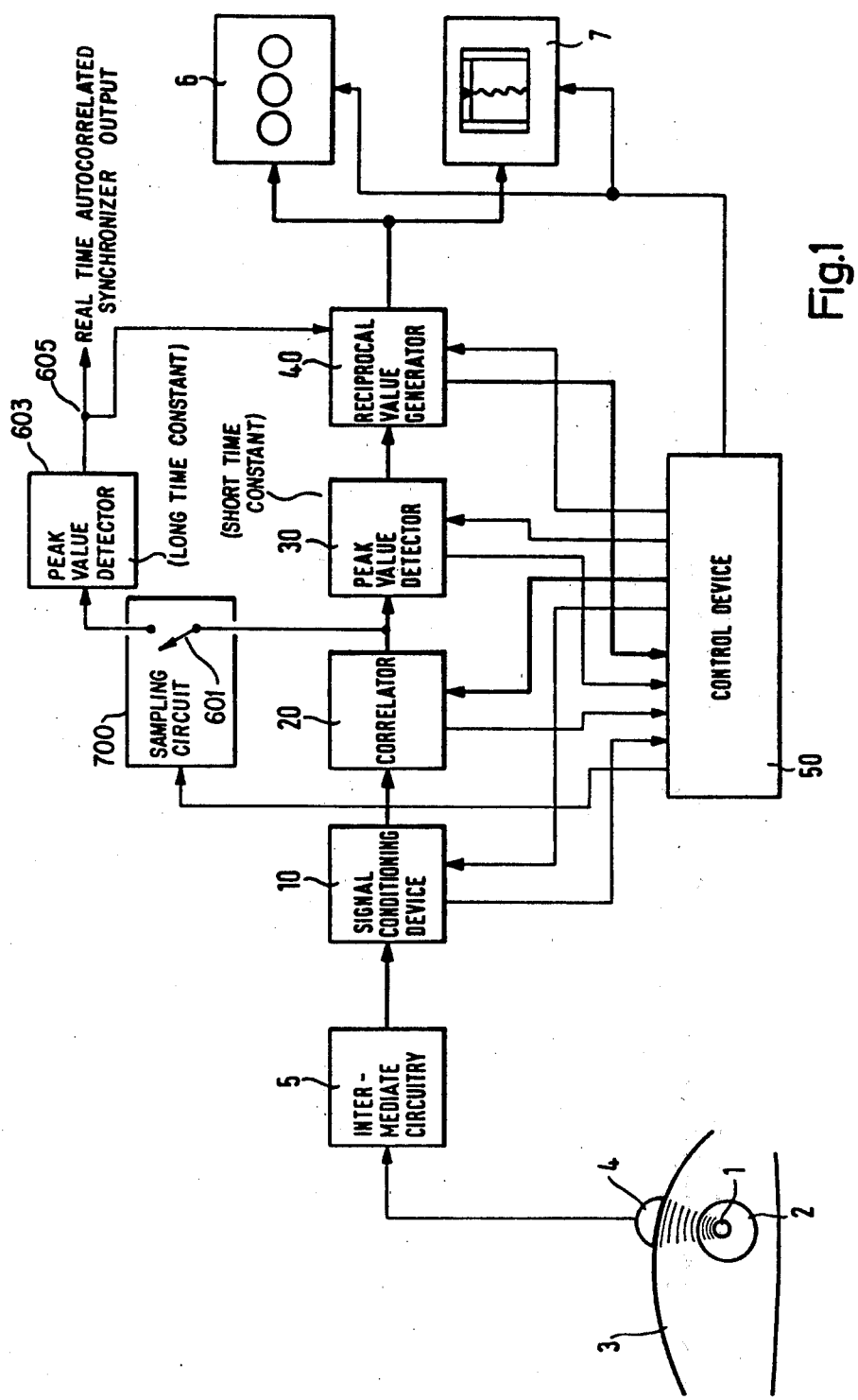
FIG. 1 is the entire block diagram of a device for period or frequency measurement.

In FIG. 1, there is a schematic representation of the heart 1, of a fetus 2, in the uterus. The number 4 represents an ultrasonic pick-up, which receives the ultrasonic signals reflected by the heart 1, and, via a suitable circuitry 5, passes these signals to a signal conditioning device 10. For the sake of simplifying the representation, the ultrasonic emitter, the frequency of which is, in this example 2.1 MHz, is not represented. The signal conditioning device 10 is described in more detail below.

The signal conditioned in the signal conditioning device 10 is passed on to the correlator 20, which feeds an autocorrelation curve to a peak value detector 30, which measures the interval between the initial peak value and the first important peak value of the autocorrelation curve. The signal representing this interval is fed into a reciprocal value generator 40, which from the time signal, produces a signal corresponding to the heartbeat rate. The correlator 20, the peak value detector 30, and the reciprocal value generator 40 are described in more detail below.

The signal corresponding to the heartbeat rate is fed to a display 6 and a printer (recorder) 7, by which it is visually displayed and recorded, respectively.

50 designates a control device which, as is described below, responds to certain conditions in the circuitries 10, 20, 30 and 40, by effecting an appropriate adjustment or optimization of certain parameters in these circuitries. The control device 50 also switches off the display 6 and the recorder 7, if the conditions established indicate that an erroneous display or recording would otherwise be effected.

Figure 2:
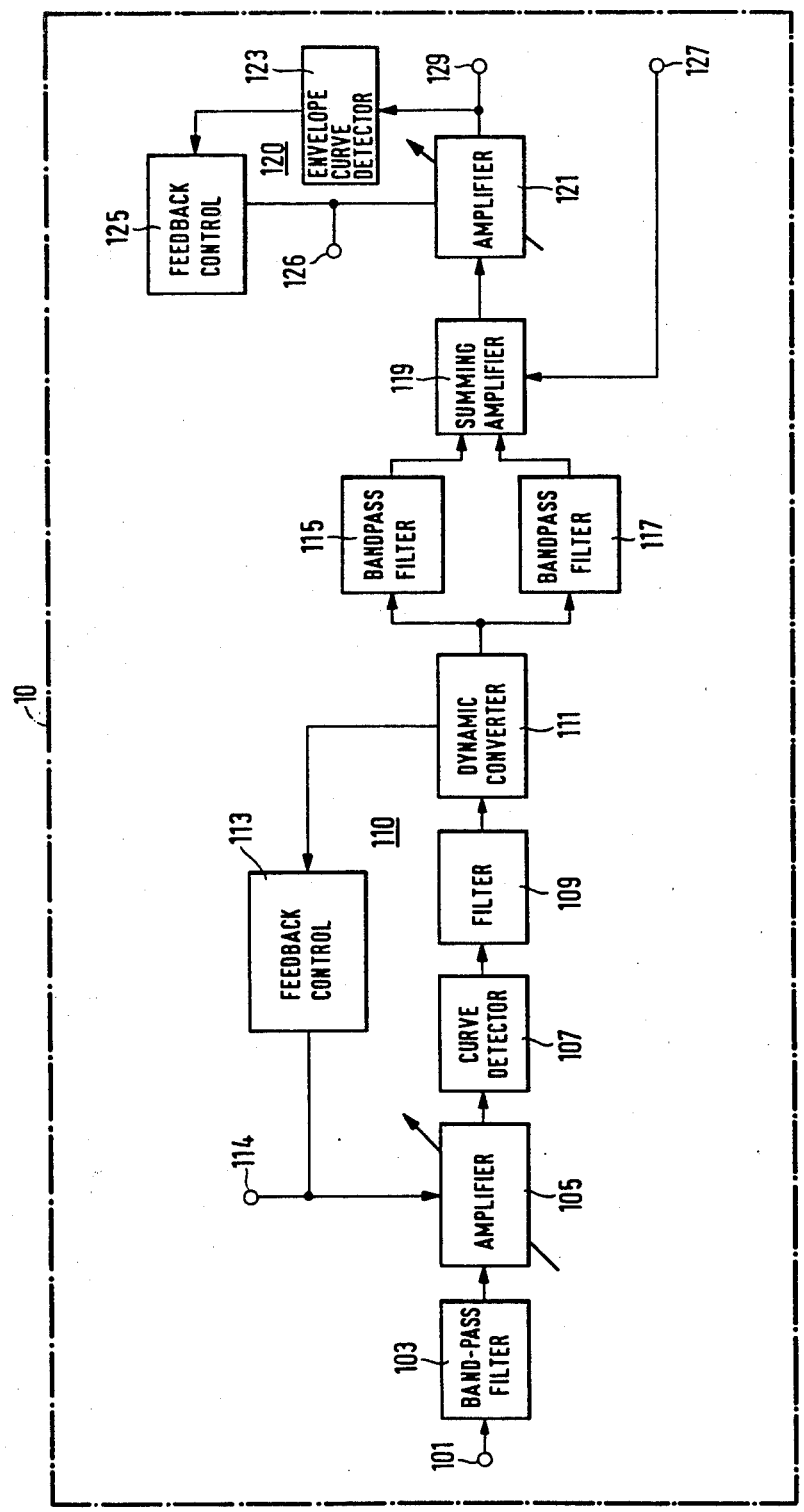
FIG. 2 is a detailed block diagram of the signal conditioning device contained in FIG. 1.

FIG. 2 is a block diagram of the signal conditioning device marked 10 in FIG. 1. The input signal 101 is first fed through a band-pass filter 103, which in the present example allows a frequency range of 300 to 1000 Hz to pass, so that the valve signal is passed completely, while the bloodflow signal and the muscle signal are completely or partially suppressed. The output signal of the band-pass filter 103 is amplified in an amplifier 105, with a voltage-controlled gain, rectified in an envelope curve detector 107, smoothed in a filter 109 and then fed to a non-linear dynamic converter 111. The components 105, 107, 109 and 111 together with a feedback control 113 form a first control loop 110. The amplifier 105 is driven by an opto-electronic component in such a way that its gain depends upon the feedback signal in a manner that approximately corresponds to a negative exponential function.

The filter 109 is, preferably, a low-pass filter having an upper cutoff frequency of 50 to 70 Hz, so that the audiofrequencies are largely filtered out.

The non-linear dynamic converter 111 is a quasi logarithmic converter which expands the low amplitudes of the input signal and compresses the larger amplitudes. This has the advantage that the structure of the signal is improved for the subsequent autocorrelation since, for autocorrelation, the emphasizing of the peak values of the input signal is not so important as, rather, the similarity of the overall structure of the signal from one period to another.

The output signal of the dynamic converter 111 is also fed to the feedback control 113 for the production of the feedback signal of the first control loop 110. Since the negatively exponential behaviour of the amplifier 105 and the logarithmic behaviour of the dynamic converter 111 cancel each other out, the result is a linear control behaviour. The output signal of the dynamic converter 111 is thus kept essentially constant for any input level.

In the present embodiment, the effective time constant of the first control loop 110 is between 1.5 and 2.2 sec, that is, it is larger than the largest heartbeat period. It is thus ensured that the shape of the curve during a period is in no way impaired by the control process. Only differences in level between successive periods are control-compensated.

The output signal of the dynamic converter 111 is fed to two different bandpass filters 115 and 117, which output signals are mixed again with variable coefficients in a summing amplifier 119.

The bandpass filters 115 and 117 allow the frequency ranges between 15 and 50 Hz and 3.3 to 15 Hz respectively to pass. Thus, the basic rate of the fetal heartbeat which lies between 0.8 and 3.5 Hz is suppressed. This is, however, not associated with any problems, since the complete information on the periodicity is available in each range of the frequency spectrum. Non-suppression of the basic rate would, however, be critical since the basic rate with its high level could cause the correlator to go into saturation.

The output signal of the summing amplifier 119 is fed to a second control loop 120, which similarly to the first control loop 110, comprises an amplifier 121 with voltage-controlled gain, an envelope curve detector 123 and a feedback control 125. In this way, at the output 129 of the signal conditioning device a signal, very constant with regard to level, is produced. The feedback signals of the two control loops 110 and 120 are available for pick-up at the outputs 114 and 126 and are processed by the control device described below in connection with FIG. 8.

Figure 3:
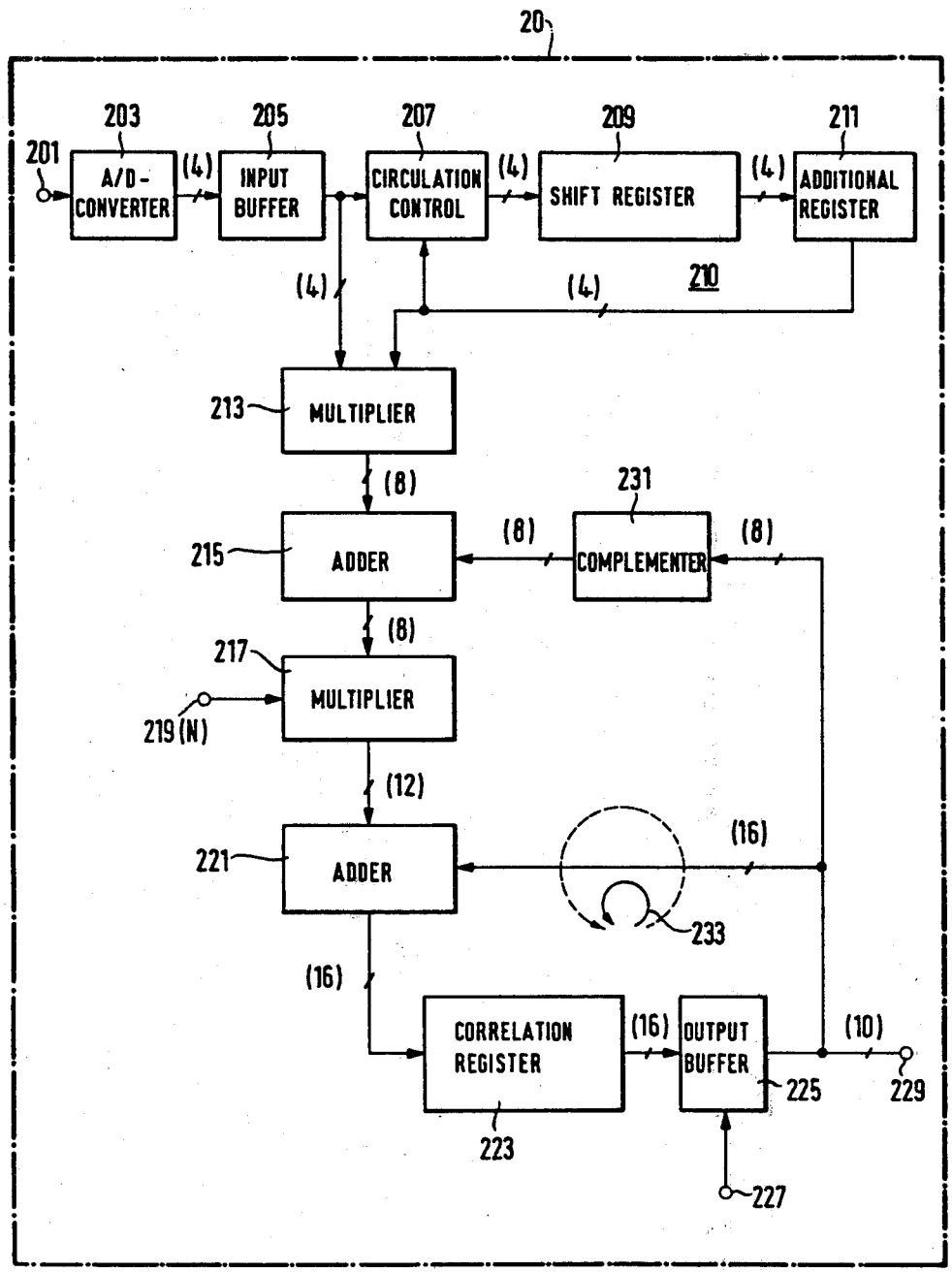
FIG. 3 is a block diagram of the correlator contained in FIG. 1.

In FIG. 3 the block diagram of the autocorrelator marked 20 in FIG. 1 is represented. The input terminal 201 is connected with the output terminal 129 (FIG. 2). The analog input signal picked up at this point is converted into a series of digital signals in an analog/digital converter 203; in this example these signals are two's complement binary numbers with a fixed decimal point and a length of four bits (one sign bit and three digit bits).

The output signal of the analog/digital converter 203 is fed on the one hand to a shift register 209 via an input buffer 205 and, on the other hand to a first multiplier 213. The shift register 209 can accommodate 256 four-bit words. Together with an additional register 211 for one word and a circulation control 207, a circulation loop 210 for 257 words is formed. If a circulation of 256 words is considered as one circulation period, the circulation loop 210 appears to shift its contents by one step per period. Following each cycle, a new data word is fed into the first storage location instead of the oldest data word arriving there.

In the case just described the scanning frequency is 200 Hz which corresponds to a scanning period of 5 ms. When the circulation loop circulates between two scanning points in 256 steps, a clock time of 19.6 $\mu$s corresponding to a frequency of 51.02 kHz results.

The first multiplier 213 forms products out of the data words contained in the shift register 209 and the data word contained in the input buffer 205. For each circulation the entire contents of the shift register 209 appears, one word at a time at the circulation control 207. The contents of the input buffer 205, however, do not change during this time. Thus the product $$P_{(n,k)} = D_n \cdot D_{(n-k)} \tag{1}$$

is obtained as the output signal of the multiplier 213 for the k-th step of the n-th circulation period. k can also be considered to be the logical storage location of the data register, and n can be regarded as the real time. D represents the four-bit-long data words and P is the maximum eight-bit-long product.

If these magnitudes $P_{(n,k)}$ for each k are integrated over a certain period, the autocorrelation for each k is then obtained. If, however, the requirement was the processing of all P values, a very large store would be needed. By means of the exponential integration described below, such a large store has been obviated.

A first adder 215 adds the output value of the first multiplier 213 to the complement of each "old" correlation value in a correlation register 223. The correlation value is fed via an output buffer 225 and a complementer 231 to the first adder 215. The output value of this latter is $$S_{(n,k)} = P_{(n,k)} - C_{(n,k)} \tag{2}$$

where C is the correlation value and S the intermediate total.

In a second multiplier 217 the intermediate sum $S_{(n,k)}$ is multiplied by a positive constant preset at an input 219, the constant here being assumed to be $\frac{1}{2}^N$. This has the advantage of permitting the second multiplier 217 to be designed as a simple data multiplexer, as long a N is a natural number.

The output value of the second multiplier 217 is in a second adder 221 added to the actual "old" correlation value in the correlation register 223. As can be seen in FIG. 3, the second adder 221, the correlation register 223 and the output buffer 225 together form a circulation loop 233. A second circulation loop includes in addition the complementer 231, a first adder 215 and the second multiplier 217. These two loops circulate synchronously with the circulation loop 210. For the correlation values in the loop 233 the following applies:

$$C_{(n+1,k)} = C_{(n,k)} + \frac{1}{N} \{P_{(n,k)} - C_{(n,k)}\} \quad (3)$$

$$= \left(1 - \frac{1}{2^N}\right) C_{(n,k)} + \frac{1}{2^N} \{D_n \cdot D_{(n-k)}\}$$

The upper form of the equation represents the relation between two consecutive values at the output 229, while the other form reproduces the overall relationship between the data and the correlations. It can be seen that the "old" correlations in the correlation shift become smaller at a time constant determined by N and that the added new products "freshen" up the existing correlation values. If the equation (3) is integrated (summated), the following results:

$$C_{(n,k)} = \frac{1}{2^N} \sum_{m=0}^{\infty} \left(1 - \frac{1}{2^N}\right)^m \cdot \{D_{(n-m)} \cdot D_{(n-m-k)}\} \quad (4)$$

Provided that N is large, this equation corresponds to the analog autocorrelation integral $$F_{(t_0, \tau)} = \frac{1}{\alpha} \int_{t=t_0}^{-\infty} f(t) \cdot f(t - \tau) \exp\left(-\frac{t}{\alpha}\right) dt \quad (5)$$

where
F = the autocorrelation
f = the signal under investigation
$\alpha$ = the equivalent data length (time constant)
$t_0$ = the real time
t = the integration parameter and
$\tau$ = the time shift.

If the equations (4) and (5) are compared with each other, the following is obtained for the equivalent data length $$T_{eq} = \alpha = m_{eq} \cdot (5 \text{ msec}) \quad (6)$$

Provided that N is large, the following applies:

$$m_{eq} = 2^N \text{ or } N = \log_2 m_{eq} \quad (7a, 7b)$$

From the equations (6), (7) the following table can be derived:

| N | $m_{eq}$ | $T_{eq}$ |
| --- | --- | --- |
| 5 | 32 | 160 ms |
| 6 | 64 | 320 ms |
| 7 | 128 | 640 ms |
| 8 | 256 | 1.28 s |
| 9 | 512 | 2.56 s |

For the possible fetal heartbeat period (283 to 1250 ms, corresponding to 48 to 212 beats per minute), the suitable values of N are accordingly 6, 7 or 8. Within the range of these values KN can change from one period to another.

At the output 229 of the correlator represented in FIG. 3, its entire register contents appear every 5 ms for all values of time shift. The signal at the output 229 can, after conversion into an analog form, be visualized on the screen of an oscilloscope as an autocorrelation curve when the oscilloscope is triggered every 5 ms in accordance with the circulation period.

The output buffer 225 has a re-set input 227 with the aid of which the contents of the circulation loop 223 can be completely or partially erased.

The correlator, represented by FIG. 3 is largely identical, both in design and function, with the Hewlett-Packard correlator model 3721A.

Figure 4:
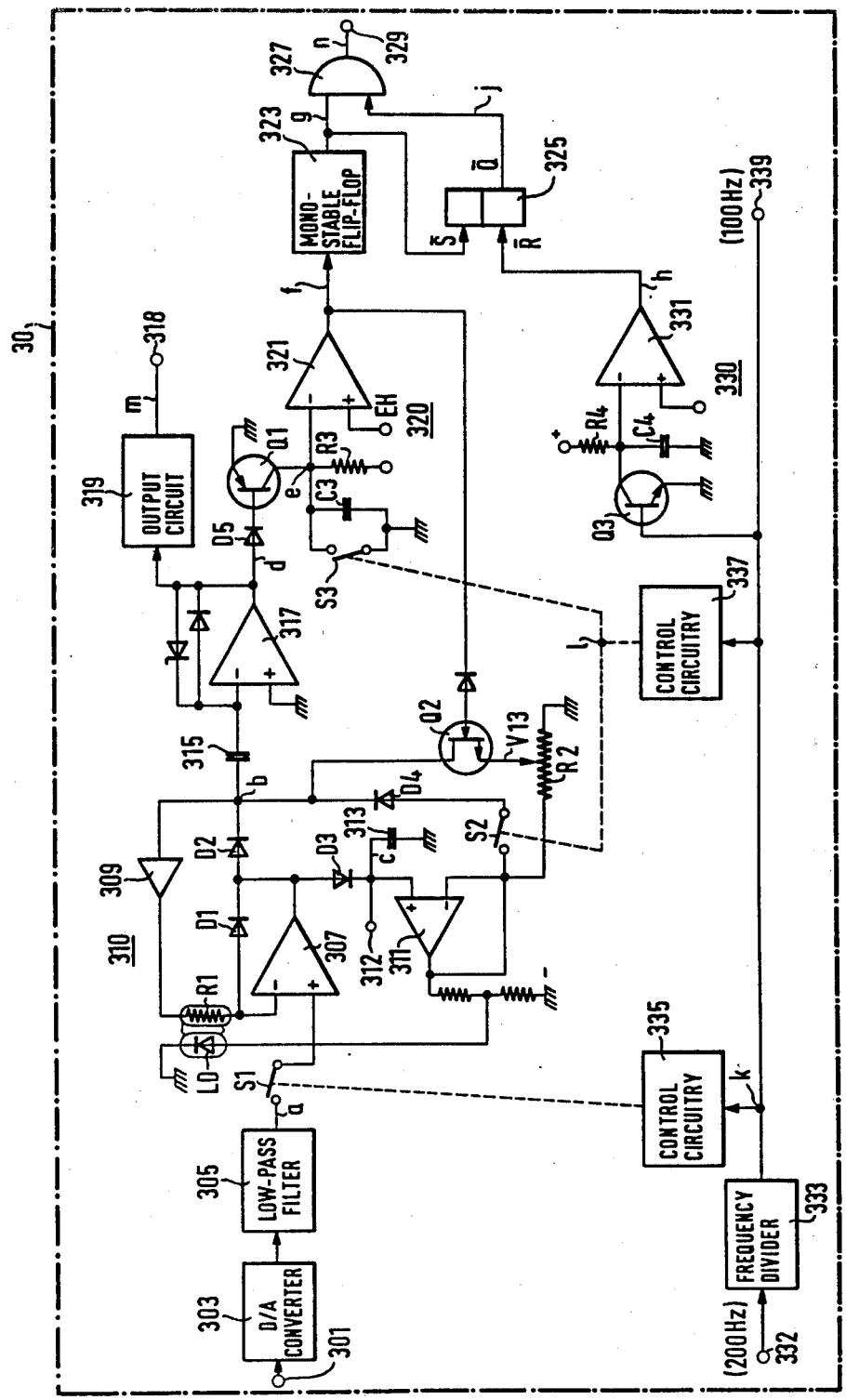
FIG. 4 is the block diagram of the peak value detector contained in FIG. 1.

In FIG. 4 the circuitry of the peak value detector marked 30 in FIG. 1 is represented. The input terminal 301 is connected to the output 229 of the correlator. The signal arriving there is first converted into an analog curve in a digital/analog converter 303 and then smoothed in a low-pass filter 305.

A clock frequency of 200 Hz is fed into a further input 332; this frequency is halved in a frequency divider 333 to 100 Hz. This halved frequency is used to drive a switch S1 via a control circuitry 335. During each odd circulation period, the switch S1 allows the autocorrelation curve to pass through to an amplifier 301, but blocks it during each even circulation period.

In the amplifier 310 the peak value of the incoming signal is fed to two holding capacitors by an operational amplifier 307. In addition a feedback is effected via a feedback amplifier 309 to the input of the operational amplifier 307. The feedback and thus the control of the overall gain of the amplifier 310 is effected via a control loop, which contains an operational amplifier 311 and an opto-electronic component LD, R1.

On account of its connection to the input of an operational amplifier 317, the capacitor 315 is virtually at ground while the capacitor 313 has a direct connection to ground. The voltages across the two capacitors follow the output voltage of the operational amplifier 307 as long as this is rising. Owing to the diodes D2 and D3 however, the voltage at the capacitors 313 and 315 does not drop when the output voltage of the operational amplifier 307 falls.

The discharge time constant of the capacitor 313 is considerably longer than the repetition period of the signal (10 ms) but shorter than the heartbeat period. As a result, not distortions occur in the autocorrelation curve, but an amplitude control for successive heartbeat periods is possible.

The voltage at the capacitor 313 can thus be considered as the highest peak value of the current correlation curve. The moment of the highest peak value is determined in the following manner. A control circuit 337, fed by the halved clock frequency of 100 Hz, closes the switches S2 and S3 for a very short time interval at the beginning of each clock pulse period. At these moments, the voltage at the capacitor 313 is applied to the capacitor 315 via the operational amplifier 311 and a diode D4. The switch S3 effects the re-setting and activation of a time element 320. The time element 320 is provided with a capacitor C3 which is continuously charged from the moment of activation. A comparator 321 initially remains at its lowest output level and renders a field-effect transistor Q2 non-conductive so that the charging of the capacitor 315 is not influenced. As soon as the capacitor C3 has attained the threshold value of the comparator 321 however, this latter moves to a higher output level with the result that the transistor Q2 conducts and the capacitor 315 begins to discharge. This discharging, however, proceeds only until a certain voltage given by a voltage divider R2 and representing some 70 to 85% of the voltage "held" by the capacitor 313 has been attained. In this way it is ensured that the peak value detector does not respond to smaller peaks found between the main peaks, the distance between which is to be measured.

The re-setting and activation of the time element 320 can be effected, not only by the switch S3, but also by means of a transistor Q1. This is the case whenever the output signal of the operational amplifier 307 attains a peak value which exceeds the holding voltage at the capacitor 315. When this happens, a polarity detector 317 makes the transistor Q1 conductive, so that as a result the transistor Q2 does not conduct and the charging and holding sequence of the capacitor 315 is not influenced.

The end of the charging period corresponds to the position of the main peak value, although the autocorrelation curve around this peak value manifests a number of smaller peak values. Ignoring a certain time delay, the moment is indicated by the switchover of the output signal of the comparator 321. The time delay of the present example is 1 ms, corresponding to 256 ms of the real time signal.

Figure 5A:
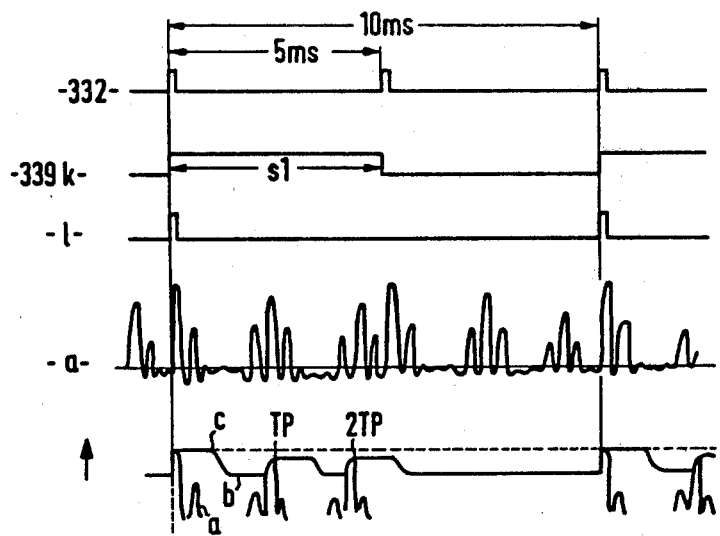
FIGS. 5A and 5B are curves serving as an explanation of the mode of functioning of the peak value detector shown in FIG. 4.
Figure 5B:
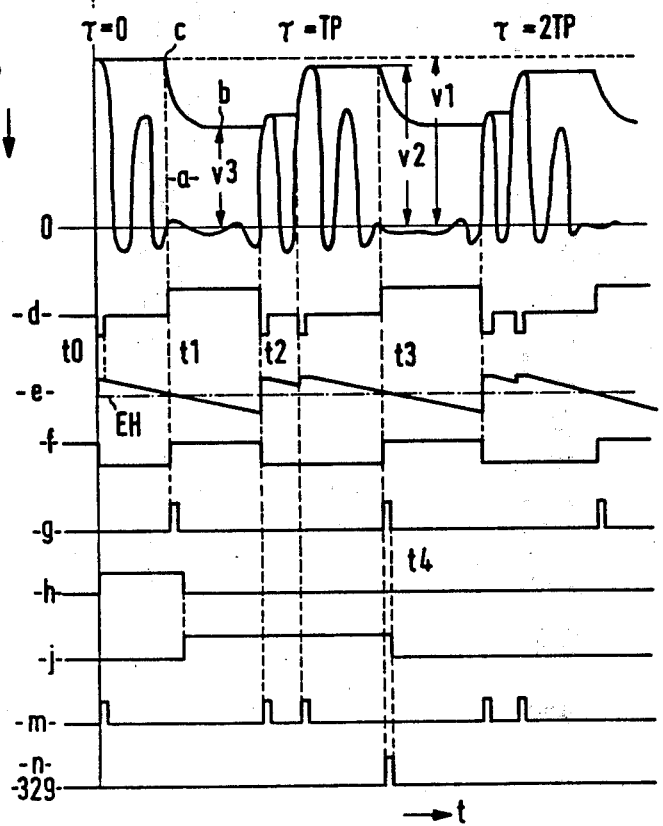

In FIG. 5 the signal variations at the points marked a to n in FIG. 4 are represented. In can be seen that the second switchover time $t_3$ of the time element 320 (the first switchover corresponds to the initial peak value of the actuation of the switch S2) corresponds to the position of the main peak value of the autocorrelation curve. With the aid of a monostable flipflop 323 (FIG. 4), a pulse g is produced which is fed to the output terminal 329 of the peak value detector via an AND gate 327. The trailing edge of the pulse g causes the setting of a flipflop 325 which, in its turn via a signal j blocks the AND gate to further pulses corresponding to the subsequent peak values of the autocorrelation curve. The flipflop 325 can be re-set by means of a further time element 330. The re-setting moment has been selected in such a way that it lies shortly after the initial peak value. The output signal d of the polarity detector 317 can, via an output circuit 319, also be picked up at an additional output 318 as signal m.

In its design and mode of operation, the peak value detector described above corresponds essentially to the peak value detector described in the German Laid-Open Patent Application 2 143 971. In comparison with this latter, however, it has been modified in that it does not directly scan a given signal curve in real time, but the autocorrelation curve in an abbreviated time scale.

Apart from this, the measurement is effected from the origin as determined by the time generator to the first main peak value and not between two peak values. Since a compressed time scale is employed, that is up to 256 measurements are carried out between one heartbeat and the next, erroneous measured values can be eliminated during the current heartbeat period and replaced by better values, while in the case of a real-time-measurement, a new measured value cannot be obtained until the following heartbeat period.

In FIG. 3 the reciprocal value generator designated 40 in FIG. 1 is represented. The associated signal variations are shown in FIG. 7.

A function generator 403 produces a 1/t hyperbola. The half clock frequency of 100 Hz present at the output 339 of the peak value detector (FIG. 4) is fed to the output 402 of the function generator 403. The generation of the 1/t hyperbola is effected in response to a pulse. At the moment of interest, this hyperbola is scanned and the scan value obtained in this way represents a direct measure of the frequency corresponding to the measured time interval. In the present example, the hyperbola is shifted with respect to the origin by a delay time of $T_d$, which corresponds to the delay time of the time element 320 (FIG. 4). In order to avoid unnecessarily high coordinate values of the hyperbola, the function generator 403 also remains at a constant value for a time period of $T_o$ before it begins to generate the hyperbola.

The signal n at output 329 of the peak value detector (FIG. 4) is fed to the input 401 of the reciprocal value generator. A time window generator 407 drives a gate circuit 409 which pemits the signal n to pass only during the expected pulse times, a deviation of ±25 heartbeats per minute being permissable.

Figure 7:
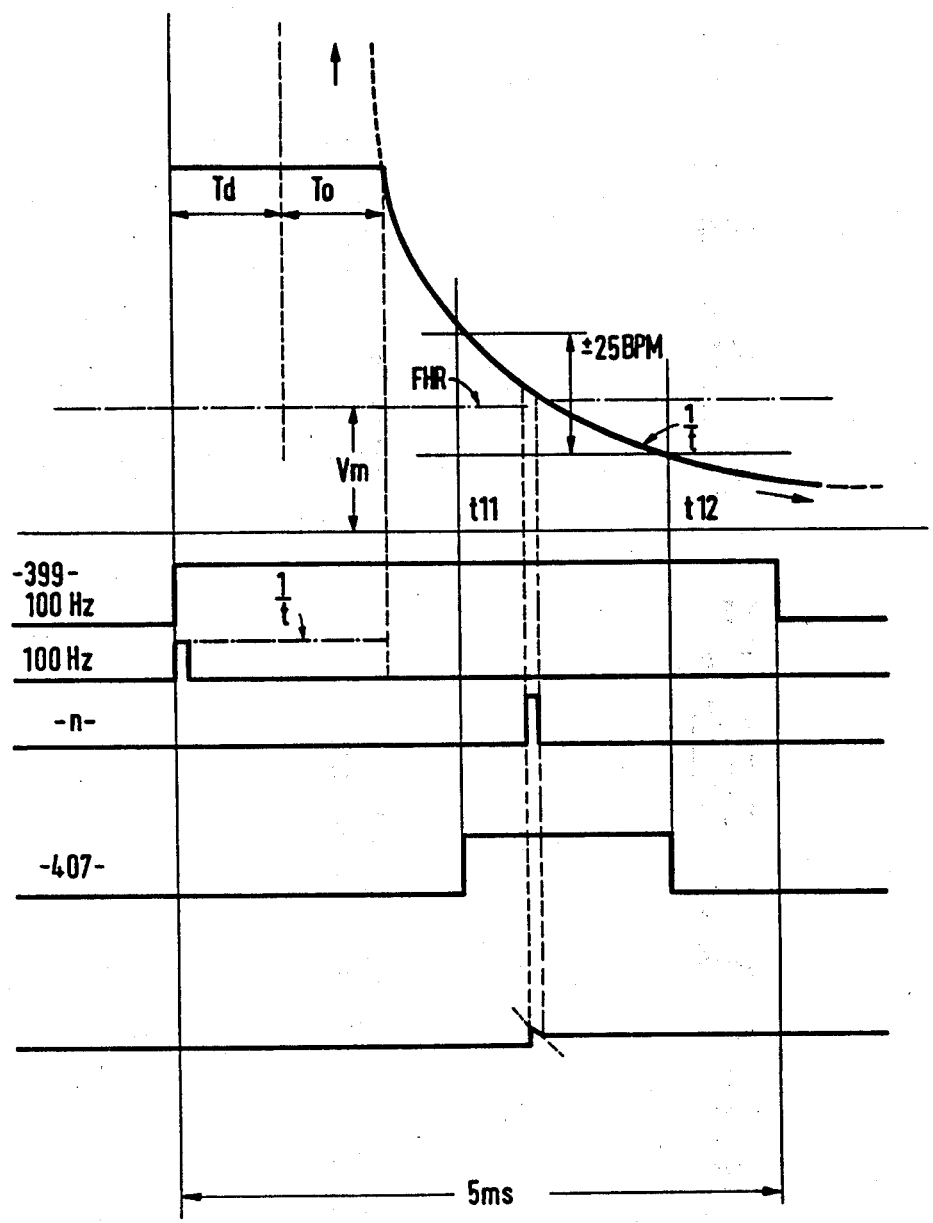
FIG. 7 are curves serving as an explanation of the mode of fuctioning of the circuitry shown in FIG. 6.

The opening and closing moments of the time window are designated $t_{11}$ and $t_{12}$ in FIG. 7. In its turn, the time window generator 407 is controlled by the measured frequency value which, in order to increase stability, is passed via a low-pass filter 415. An error detector 417 is activated if, during the time window, no pulse passes through the gate circuit 409 and then gradually increases the width of the time window.

A scanning circuitry 405 scan the hyperbola value corresponding to the moment of passage of a pulse through the gate circuit 409 and holds this value. A limiter 411 limits the frequency value delivered by the scan circuit 405 to the range between 48 and 212 heartbeats per minute in order to avoid an overdriving of the display 6 or the recorder 7 (FIG. 1).

Figure 6:
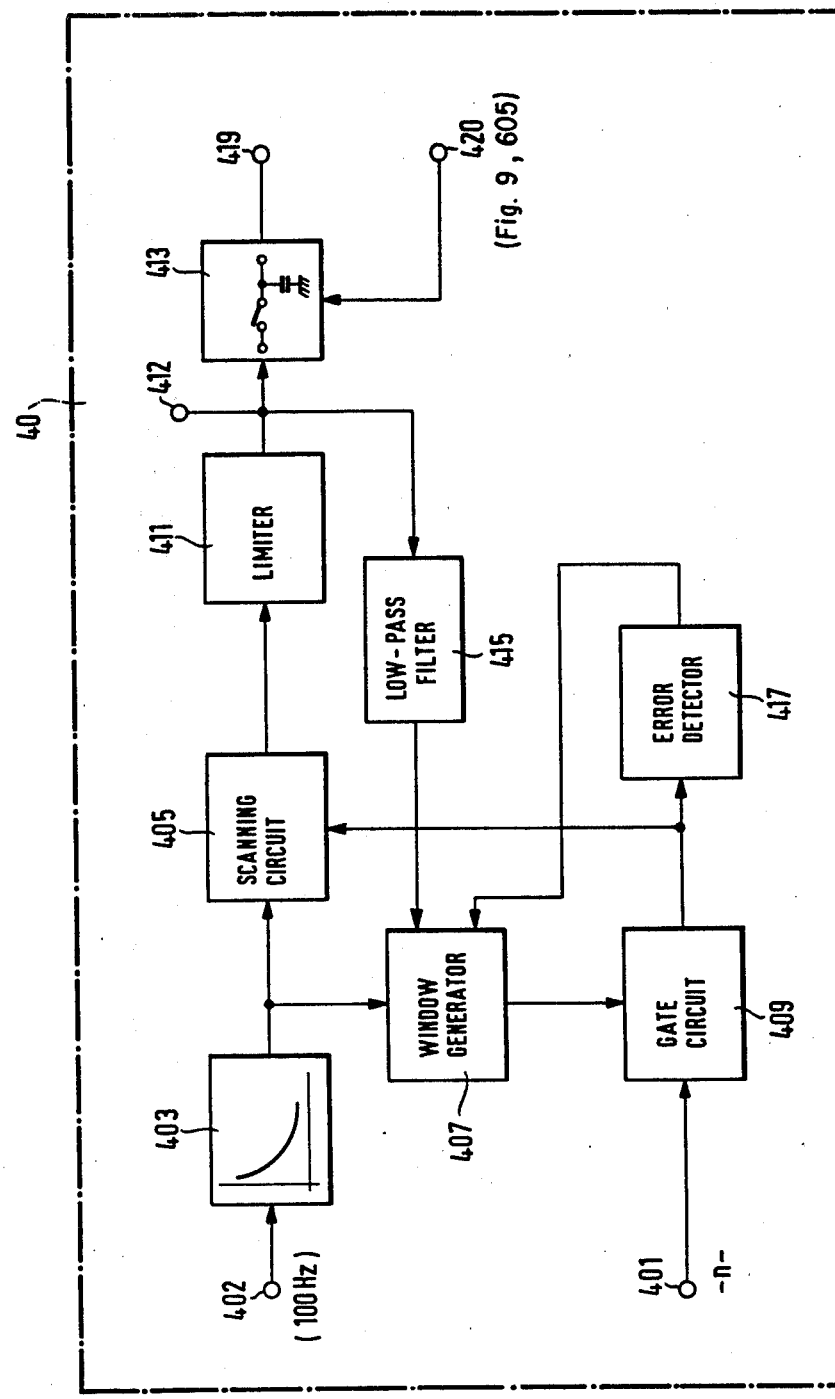
FIG. 6 is a block diagram of the computing circuitry for the determination of the signal frequency from the interval of the peak values in the autocorrelation curve.
Figure 8:
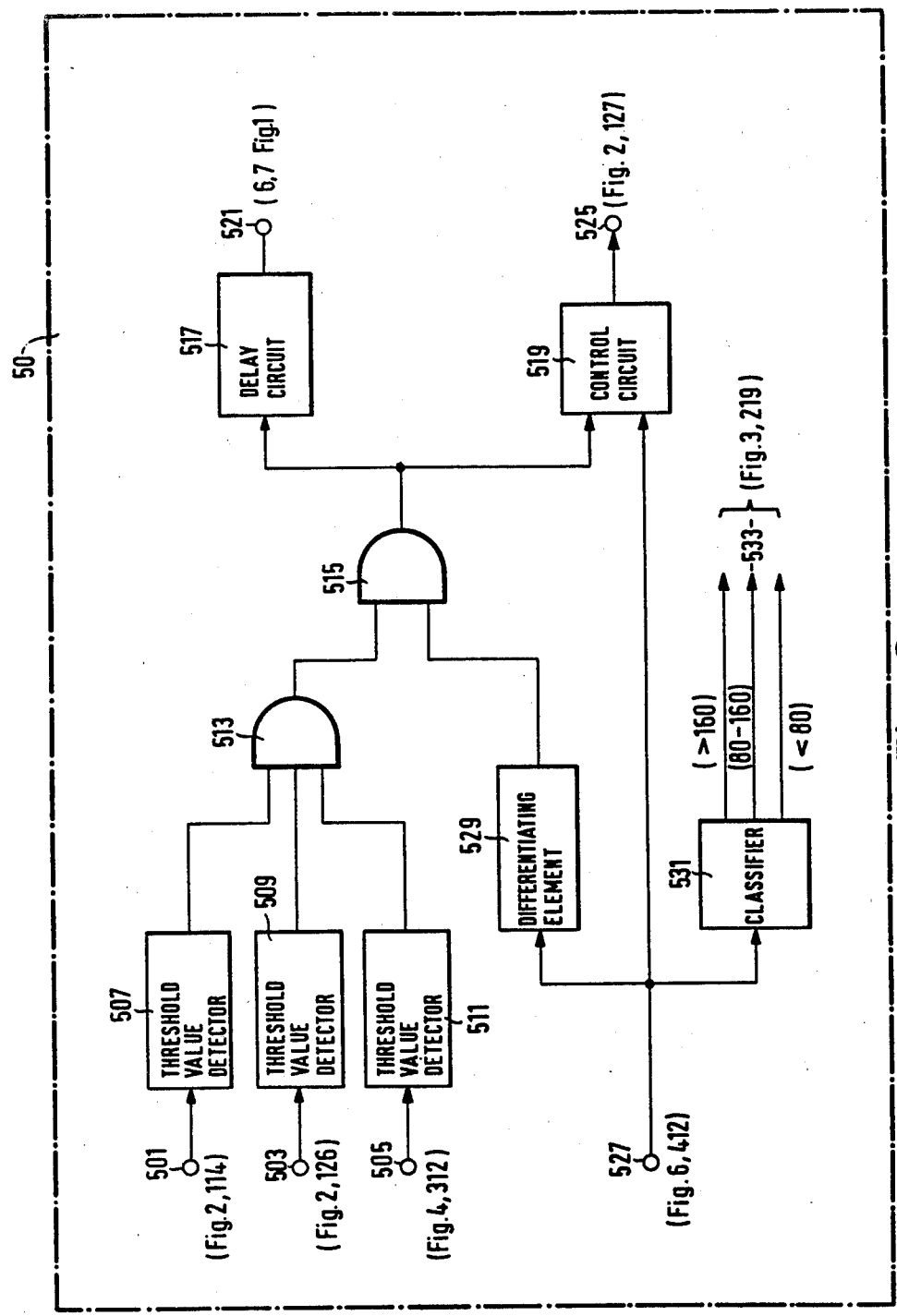
FIG. 8 is a block diagram of the control device contained in FIG. 1.

A second holding circuit 413 serves to eliminate erroneous scan values in the scan circuit 405 and, instead, to deliver the prior value at the output 419 in each case. The driving of the second scan circuit 413 is effected via an input 420 in such a manner that the value at the output 419 is updated only in response to an input signal (605 of FIG. 9). In FIG. 8 the control circuitry marked 50 in FIG. 1 is represented. Its inputs 501, 503, 505 and 527 receive the signals appearing at the outputs 114, 126, 312 and 412 of the circuits shown in FIGS. 2, 4 and 6 and at its outputs 521, 523, 525 and 533 delivers control signals to the devices 6 and 7 (FIG. 1) and the inputs 420, 127 and 219 (FIGS. 6, 2 and 3). By means of the control signals, the individual system parameters in accordance with the conditions established, are either optimized or, if this is not possible, alarm signals are delivered or the display and recorder switched off.

The signals at the outputs 114 and 126 (FIG. 2) and 312 (FIG. 4) are fed to threshold value detectors 507, 509 and 511, which deliver an output signal only when their input signal exceeds a certain threshold value. An AND gate 513 delivers via its output a logical 1 when all three threshold detectors deliver an output signal. In all other cases, the output signal of the AND gate 513 is a logic 0. The output signal of the AND gate 513 represents an initial test parameter for the validity of the measurement being carried out.

In addition, a test device can also be provided for the signal-to-noise ratio of the measuring signal, this device providing an indication when the periodic component of the measuring signal is virtually non-existent.

A further condition to be checked is the rate of change of the computed heartbeaut frequency. This check is carried out by means of a differentiating element 529 to which the signal arriving at the output 412 (FIG. 6) is fed via an input 527. If the peak value detector has responded to an "incorrect" peak value, or when no peak value was present, the heart rate undergoes a sudden, very marked change within 10 ms. Since the actual heartbeat rate cannot change within a heartbeat period (cycle), such a change of frequency indicates an error. Thus, the differentiating element 529 delivers a logic 0 at its output when such an error occurs, while normally it delivers a logic 1. The AND gate marked 515 thus delivers a logic 1 at its output only when all test conditions are found to be in order.

Via a delay circuit 517 and an output 421, the output of the AND gate 515 continues to be connected to the display 6 and the recorder 7 (FIG. 1) and switches these latter off when, after a given time delay (in the present example some 1.2 sec) an error state continues to exist. In this way, temporary errors are ignored.

Finally, the output signal of the AND gate 515 together with the signal at the input 521 is fed to a control circuit 519 for the coefficient matrix 119 shown in FIG. 2.

Lastly, the heart rate signal arriving at input 527 is by a classifier 531 placed in one of three ranges to which various values of N (FIG. 3) are assigned in the following manner:

| Heartbeat rate (beats per minute) | N |
|---|---|
| above 160 | 6 |
| 80–160 | 7 |
| below 160 | 8 |

The corresponding signals are fed to the input, marked 219 in FIG. 3 of the multiplexer 217 via an output 533.

Figure 9:
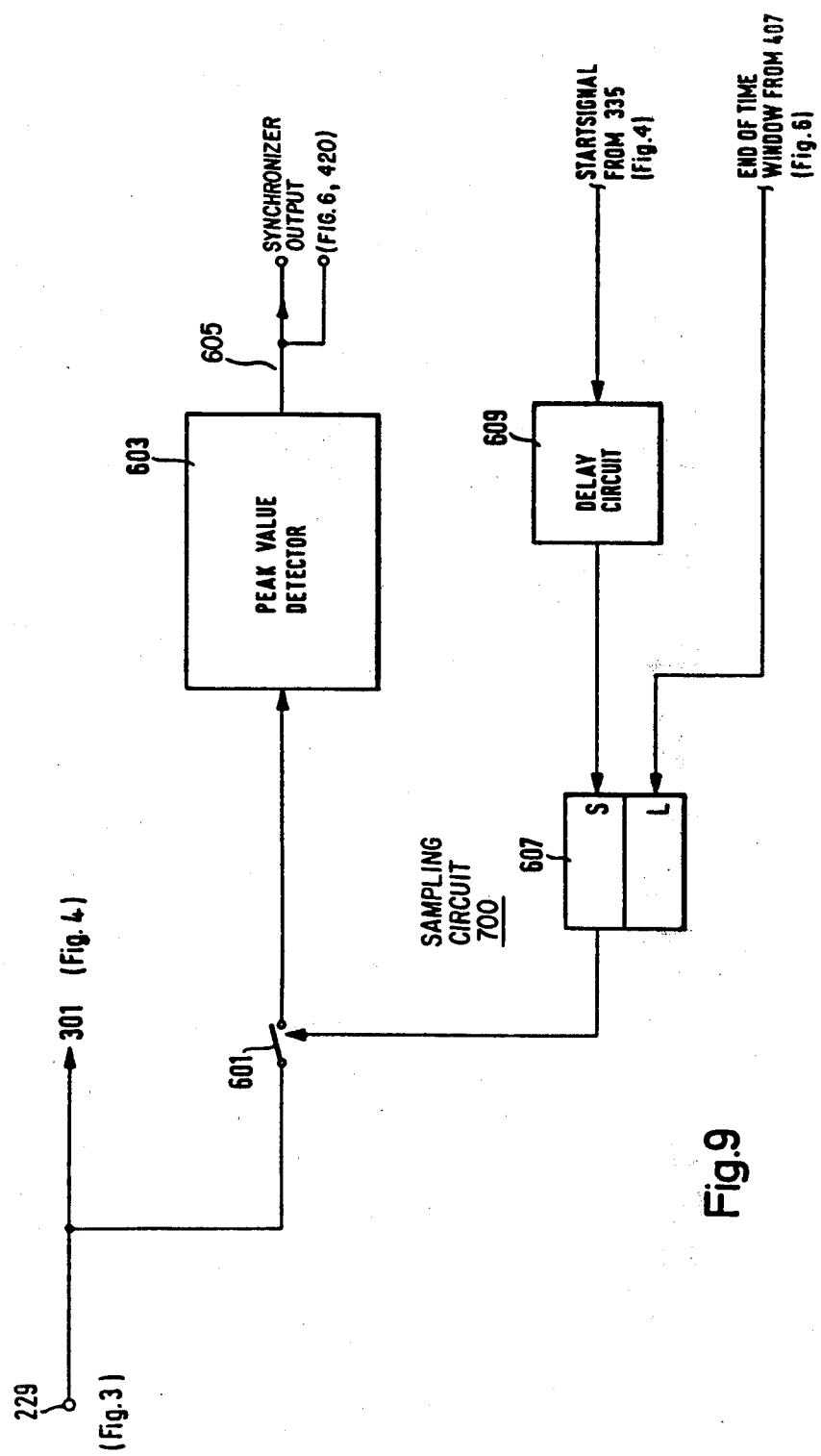
FIG. 9 is a block diagram of an output circuit for beat display.

FIG. 9 indicates how, in accordance with the invention a heartbeat display can be derived from the autocorrelation curve. The signal at the output 229 (FIG. 3) of the correlator 20, is, via switch 601, additionally fed to a peak value detector 603. The peak value detector 603 has, in principle, the indentical design as the peak value detector 30 shown in FIG. 4. The holding time of the peak value detector 603 is, however, considerably longer than that of the peak value detector shown in FIG. 4. It is somewhat less than the smallest period to be measured. The peak value detector 603 delivers a signal at its output 605 when, at the input 201 (FIG. 3) of the correlator 20 a new heartbeat appears since it is always at this point that the time maximum of the peak value of the autocorrelation curve following the original peak value occurs.

The switch 601 is driven in such a way that only the relevant part of the autocorrelation curve about the main peak value "runs" over the peak value detector 603. The control of the switch is effected via a flipflop 607 which, when it has been set, keeps the switch closed but otherwise leaves it open. The setting of the flipflop 607 is effected via a delay circuit 609 by means of the start signal of the control circuit 355 (FIG. 4). The flipflop 607 is cancelled by the end of the time window signal of the time window generator 407 (FIG. 6). The delay time of the delay circuit 609 is somewhat smaller than the smallest possible period to be measured divided by 200, in accordance with the scan frequency of 200 Hz. Thus, during a real-time period some 100 peak values enter the peak value detector 603 corresponding to the number of output autocorrelation curves appeating at the output 229 (FIG. 3). The highest peak value of these then effects a response of the peak value detector 603.

The circuitry described has the advantage that a phase-correct output of the heartbeat at output 605 is possible, while at the same time, the favourable signal-to-noise ratio of a continuous correlation is retained. In this way, a very high trigger reliability is obtained when the signal at the output 605 is used as the enable signal for the frequency output which can be effected by inputting this signal at the input 420 (FIG. 6).

We claim:

1. Apparatus for approximating in real time by autocorrelation the consecutive occurrences of a generally periodic but unknown signal from a signal source, the apparatus comprising:

signal collection and conditioning means for acquiring the unknown signal from the signal source and enhancing selected spectral components thereof to produce a conditioned signal;

autocorrelation means coupled to the conditioned signal for repetitively producing compressed time scale sequences of autocorrelation amplitude values describing a plurality of cyclic variations, each sequence corresponding to at least one period of the unknown signal and including both an initial peak value for an initial cyclic variation whose amplitude is the highest amplitude within the sequence and a consecutive next peak value for a subsequent cyclic variation of amplitude less than the initial cyclic variation and wherein the amount of separation in the compressed time scale between the initial and next peaks corresponds to the period of the unknown signal; and peak value detection means coupled to the sequences of autocorrelation amplitude values for detecting within first periods each at least as long as the actual period of the unknown signal a periodic occurrence, among all the sequences, of a next peak value of amplitude greater than a selected percentage of the previously detected next peak value within the previous first period and for producing an output indicative thereof, the selected percentage chosen to allow detection of only one next peak value during each first period, whereby a real time approximate indication of a transition in the unknown signal is obtained.

2. Apparatus for approximating in real time by autocorrelation the consecutive occurrences of a generally periodic but unknown signal from a signal source, the apparatus comprising:

signal collection and conditioning means for acquiring the unknown signal from the signal source and enhancing selected spectral components thereof to produce a conditioned signal;

autocorrelation means coupled to the conditioned signal for repetitively producing compressed time scale sequences of autocorrelation amplitude values describing a plurality of cyclic variations, each sequence corresponding to at least one period of the unknown signal and including both an initial peak value for an initial cyclic variation whose amplitude is the highest amplitude within the sequence and a consecutive next peak value for a subsequent cyclic variation of amplitude less than the initial cyclic variation and wherein the amount of separation in the compressed time scale between the initial and next peaks corresponds to the period of the unknown signal;

first peak value detection means coupled to the sequences of autocorrelation amplitude values of identifying within each sequence the initial and next peaks therein, for producing an intermediate output indicative of the duration of a separation interval therebetween in the compressed time scale, and for producing a timing signal indicative of the occurrence of the start of that separation interval;

conversion means coupled to the intermediate output for producing an indicator output whose magnitude is an indication of the rate at which the unkown signal occurs;

delay means coupled to the timing signal for producing a delayed timing signal that is delayed from the timing signal by an amount less than the separation interval;

switch means coupled to the delayed timing signal and the sequences of autocorrelation amplitude values, for producing at a sampled output a collection of sampled autocorrelation amplitude values by passing incoming autocorrelation amplitude values representing the next peak of each sequence through to the sampled output for a preselected duration following the onset of the delayed timing signal; and second peak value detection means coupled to the collection of sampled autocorrelation amplitude values for detecting therein within first periods each at least as long as the actual period of the unknown signal a periodic occurrence of a next peak value of amplitude greater than a selected percentage of the previously detected next peak value within the previous first period and for producing an ouput indicative thereof, the selected percentage chosen to allow detection of only one next peak value during each first period, whereby a real time approximate indication of a transition in the unknown signal is obtained.

3. A method for approximating in real time by autocorrelation the consecutive occurrences of a transition in a generally periodic but unknown signal from a signal source, the method comprising the steps of:

acquiring the unknown signal from the signal source;

conditioning the acquired unknown signal by enhancing selected spectral components thereof to facilitate autocorrelation;

correlating each successive occurrence of the conditioned signal with results of previous such correlations to repetitively produce compressed time scale sequences of autocorrelation values describing a plurality of cyclic variations, each sequence including both an initial peak value for an initial cyclic variation whose amplitude is the highest amplitude within the sequence and a next peak value for a subsequent cyclic variation of amplitude less than the initial cyclic variation;

detecting periodic peak variations among the resulting series of next peak values from among the sequences to identify points in real time when a next peak value periocically exceeds a selected percentage of the amplitude of a previously detected periodic peak variation;

choosing the selected percentage recited in the detecting step such that only one periodic peak variation is detected during a period of time equal to the shortest expected period of the unknown signal; and producing upon each detection of a periodic peak variation an output signal that is thereby an approximation of a transition in the periodic unknown signal.

4. A method as in claim 3 further comprising the steps of:

deriving the frequency of the unknown signal from the results of each correlating step; and indicating a previously derived frequency only after the occrrence of an associated output signal produced by the producing step.

* * * * *

UNITED STATES PATENT AND TRADEMARK OFFICE
CERTIFICATE OF CORRECTION

PATENT NO. : 4,403,184

DATED : September 6, 1983

INVENTOR(S) : Rudiger Witt and Erich Courtin

It is certified that error appears in the above-identified patent and that said Letters Patent is hereby corrected as shown below:

Column 6, line 31, "301" should be --310--;

Column 6, line 52, "not" should be --no--;

Column 7, line 29, "of" should be --in--;

Column 8, line 23, "pemits" should be --permits--;

Column 10, lines 6-7 "appeating" should be --appearing--;

Column 12, line 42, "occrrence" should be --occurrence--.

Signed and Sealed this

Seventeenth Day of April 1984

[SEAL]

Attest:

Attesting Officer

GERALD J. MOSSINGHOFF

Commissioner of Patents and Trademarks